(12) United States Patent
Tsunoda et al.

(10) Patent No.: US 10,361,057 B2
(45) Date of Patent: Jul. 23, 2019

(54) X-RAY GENERATING APPARATUS AND RADIOGRAPHY SYSTEM

(71) Applicant: CANON KABUSHIKI KAISHA, Tokyo (JP)

(72) Inventors: Koichi Tsunoda, Yokohama (JP); Koji Yamazaki, Ayase (JP); Shuji Aoki, Yokohama (JP); Kazuyuki Ueda, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 366 days.

(21) Appl. No.: 15/216,523

(22) Filed: Jul. 21, 2016

(65) Prior Publication Data

US 2017/0032923 A1 Feb. 2, 2017

(30) Foreign Application Priority Data

Jul. 27, 2015 (JP) .................................. 2015-147365

(51) Int. Cl.

| | |
|---|---|
| *H01J 35/02* | (2006.01) |
| *H01J 35/06* | (2006.01) |
| *H01J 35/08* | (2006.01) |
| *H01J 35/12* | (2006.01) |
| *H01J 35/16* | (2006.01) |
| *H01J 35/18* | (2006.01) |
| *G01N 23/04* | (2018.01) |
| *H05G 1/06* | (2006.01) |
| *A61B 6/00* | (2006.01) |

(52) U.S. Cl.
CPC .............. *H01J 35/18* (2013.01); *G01N 23/04* (2013.01); *H01J 35/02* (2013.01); *H01J 35/025* (2013.01); *H01J 35/06* (2013.01); *H01J 35/08* (2013.01); *H01J 35/12* (2013.01); *H01J 35/16* (2013.01); *H05G 1/06* (2013.01); *A61B 6/40* (2013.01); *A61B 6/4488* (2013.01)

(58) Field of Classification Search
CPC .......... H01J 35/02; H01J 35/025; H01J 35/06; H01J 35/08; H01J 35/12; H01J 35/16; H01J 35/18
USPC ................ 378/121, 127, 130, 140, 141, 161
See application file for complete search history.

(56) References Cited

U.S. PATENT DOCUMENTS 4,811,375 A * 3/1989 Klostermann ........ H01J 35/101 378/121
4,964,148 A * 10/1990 Klostermann ........ H01J 35/106 378/121

(Continued)

*Primary Examiner* — Allen C. Ho
(74) *Attorney, Agent, or Firm* — Canon U.S.A. Inc., IP Division

(57) ABSTRACT

Provided is an X-ray generating apparatus, which includes: an X-ray generating tube configured to emit X-rays through a first window; an outer case configured to contain the X-ray generating tube and provided with a second window transmitting the X-rays at a position facing the first window; an insulating fluid with which an unoccupied space of the outer case is filled; an insulating member located between the first window and the second window and provided with an opening in an irradiation area of the X-ray through the first window; and an insulating third window removably fit into the opening of the insulating member, wherein a linear expansion coefficient of the third window is greater than a linear expansion coefficient of the insulating member, and the third window and the first window face each other via a gap through which the insulating fluid is flowable.

16 Claims, 6 Drawing Sheets

(56) References Cited

U.S. PATENT DOCUMENTS

| | | | |
|---|---|---|---|
| 6,314,161 B1 * | 11/2001 | Anno | H01J 35/101 378/125 |
| 7,499,525 B2 * | 3/2009 | Hörndler | F28F 13/125 378/130 |
| 7,949,099 B2 | 5/2011 | Klinkowstein | |
| 8,472,585 B2 * | 6/2013 | Ogura | H01J 35/08 378/111 |
| 8,517,607 B2 * | 8/2013 | Yamamoto | H05G 1/06 378/203 |
| 8,837,680 B2 * | 9/2014 | Tsujii | H01J 35/08 378/140 |
| 9,029,795 B2 * | 5/2015 | Sando | H01J 35/08 250/393 |
| 9,036,788 B2 * | 5/2015 | Ueda | H05G 1/025 250/522.1 |
| 9,048,058 B2 * | 6/2015 | Yamazaki | H01J 35/02 |
| 9,058,958 B2 * | 6/2015 | Aoki | H01J 35/04 |
| 9,070,529 B2 * | 6/2015 | Tamura | H01J 35/12 |
| 9,070,531 B2 * | 6/2015 | Ueda | H05G 1/025 |
| 9,076,627 B2 * | 7/2015 | Yanagisawa | H01J 35/16 |
| 9,117,621 B2 * | 8/2015 | Yamazaki | H01J 35/04 |
| 9,131,590 B2 * | 9/2015 | Suzuki | H05G 1/025 |
| 9,159,525 B2 * | 10/2015 | Yamazaki | H01J 35/06 |
| 9,177,753 B2 * | 11/2015 | Yamazaki | H01J 35/16 |
| 9,230,774 B2 * | 1/2016 | Yanagisawa | H01J 35/18 |
| 9,245,707 B2 * | 1/2016 | Tuohimaa | H01J 35/18 |
| 9,251,995 B2 * | 2/2016 | Ogura | G01N 23/04 |
| 9,263,226 B2 * | 2/2016 | Zhao | G01N 23/04 |
| 9,281,155 B2 * | 3/2016 | Ueda | H01J 35/18 |
| 9,281,158 B2 * | 3/2016 | Ogura | H01J 35/18 |
| 9,373,478 B2 * | 6/2016 | Tamura | H01J 35/12 |
| 9,401,259 B2 * | 7/2016 | Ukiyo | H01J 35/16 |
| 9,420,676 B2 * | 8/2016 | Chen | H05G 1/025 |
| 9,484,178 B2 * | 11/2016 | Yamada | H01J 35/08 |
| 9,508,524 B2 * | 11/2016 | Yanagisawa | H01J 35/12 |
| 9,514,910 B2 * | 12/2016 | Yanagisawa | H01J 35/20 |
| 9,524,846 B2 * | 12/2016 | Sato | H01J 35/08 |
| 9,552,956 B2 * | 1/2017 | Yanagisawa | G01N 23/04 |
| 9,570,264 B2 * | 2/2017 | Ogura | H01J 35/08 |
| 9,697,980 B2 * | 7/2017 | Ogura | H01J 35/16 |
| 9,711,322 B2 * | 7/2017 | Shimono | H01J 35/18 |
| 9,741,524 B2 * | 8/2017 | Kawase | H01J 35/18 |
| 9,818,571 B2 * | 11/2017 | Shiozawa | H01J 35/16 |
| 9,824,848 B2 * | 11/2017 | Ikarashi | H01J 35/08 |
| 9,831,058 B2 * | 11/2017 | Smith | H01J 5/22 |
| 9,887,063 B2 * | 2/2018 | Yamazaki | H01J 35/16 |
| 9,941,092 B2 * | 4/2018 | Greenland | C23C 4/123 |
| 10,014,149 B2 * | 7/2018 | Nakamura | H01J 35/06 |
| 10,062,539 B2 * | 8/2018 | Yanagisawa | H01J 35/08 |

* cited by examiner

X-RAY GENERATING APPARATUS AND RADIOGRAPHY SYSTEM

BACKGROUND OF THE INVENTION

Field of the Invention

The present invention relates to a radiography system applicable to medical equipment, a nondestructive inspection apparatus and the like, and relates also to an X-ray generating apparatus employed in the radiography system.

Description of the Related Art

A radiography system in which an X-ray generating apparatus is incorporated, irradiates a subject with X-rays from an X-ray generating apparatus, and detects the X-rays penetrating the subject with an X-ray detector. The X-ray generating apparatus used here includes an X-ray generating tube inside an outer case. The X-ray generating tube accelerates electrons emitted from an electron source by a tube voltage, and irradiates a target made of metal, such as tungsten, with the electrons to generate X-rays.

In order to generate desirable X-rays for X-ray radiography by the X-ray generating tube, it is necessary to apply the tube voltage in the range of 40 kV to 150 kV between the electron source and the target and to emit an electron beam of high energy. Therefore, a potential difference of at least several tens of kilovolts is produced between the X-ray generating tube and the outer case. As a means to withstand such a tube voltage, a configuration to fill a space between the X-ray generating tube and the outer case with an insulating member is known. Further, a configuration in which different insulating members are used between an X-ray generating tube and an outer case in an irradiation area and a non-irradiation area of X-ray is described in U.S. Pat. No. 7,949,099.

However, the x-ray generating apparatus described in U.S. Pat. No. 7,949,099 may lack durability because the insulating member of the irradiation area may be degraded and the insulating performance may be lowered when irradiated with radiation.

SUMMARY OF THE INVENTION

The present invention provides a means by which the durability of an x-ray generating apparatus may be improved.

According to an aspect of the present invention, an X-ray generating apparatus, includes: an X-ray generating tube provided with a first window transmitting X-rays and configured to emit the X-rays through the first window; an outer case configured to contain the X-ray generating tube and provided with a second window transmitting the X-rays at a position facing the first window;
an insulating fluid with which an unoccupied space of the outer case is filled;
an insulating member located between the first window and the second window and provided with an opening in an irradiation area of the X-rays through the first window; and
an insulating third window removably fit into the opening of the insulating member, wherein
a linear expansion coefficient of the third window is greater than a linear expansion coefficient of the insulating member, and
the third window and the first window face each other via a gap in which the insulating fluid is flowable.

According to another aspect of the present invention, a radiography system, includes: the above X-ray generating apparatus of the present invention;
an X-ray detector configured to detect X-ray which is emitted from the X-ray generating apparatus and passed through a subject; and
a system control unit configured to cooperatively control the X-ray generating apparatus and the X-ray detector.

Further features of the present invention will become apparent from the following description of exemplary embodiments with reference to the attached drawings.

BRIEF DESCRIPTION OF THE DRAWINGS

FIGS. 1A and 1B are schematic cross-sectional views of a configuration of an embodiment of an X-ray generating apparatus of the present invention, in which FIG. 1A illustrates an X-ray generating tube seen from a shielding member side, and FIG. 1B illustrates a cross-section of the X-ray generating tube including a tube axis.

FIGS. 2A and 2B are enlarged views of an area in which a third window and an insulating member of FIG. 1 face each other, in which FIG. 2A illustrates a state in which the X-ray generating apparatus is not driven, and FIG. 2B illustrates a state in which the X-ray generating apparatus is driven.

DESCRIPTION OF THE EMBODIMENTS

Hereafter, preferred embodiments of the present invention are described in detail with reference to the drawings. The size, material, shape, relative arrangement and the like of the components described in the embodiments do not limit the scope of the present invention. Well-known or publicly known techniques are applied to the portions that are not illustrated or described in the specification.

Figure 1A:
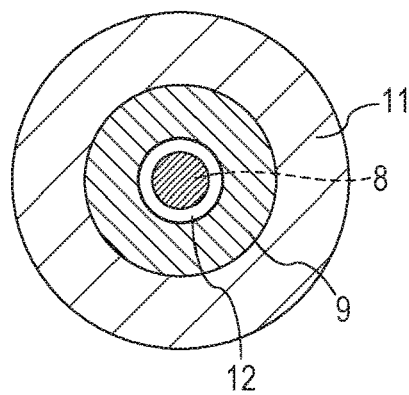
Figure 1B:
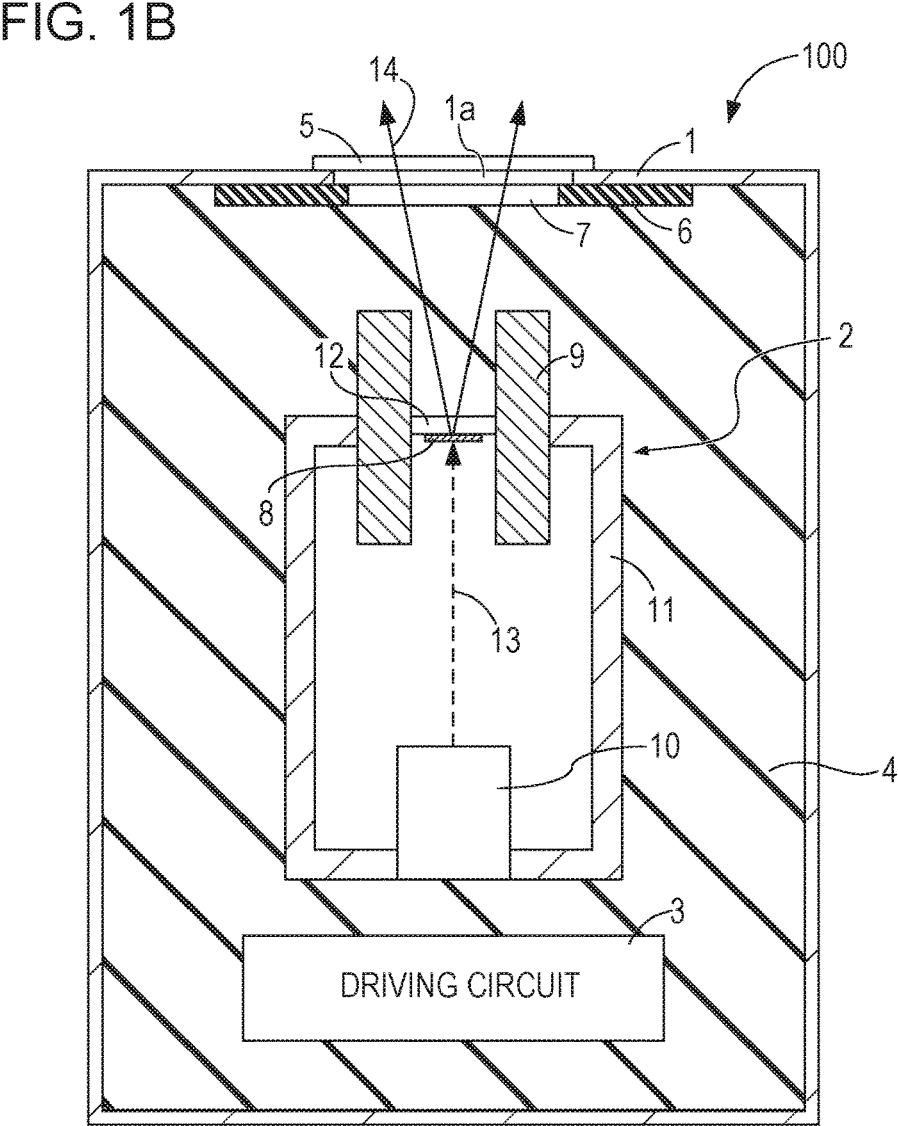
Figure 2A:
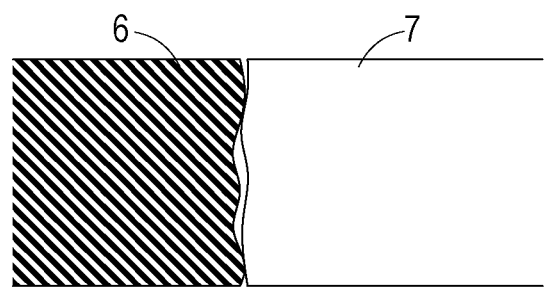
Figure 2B:
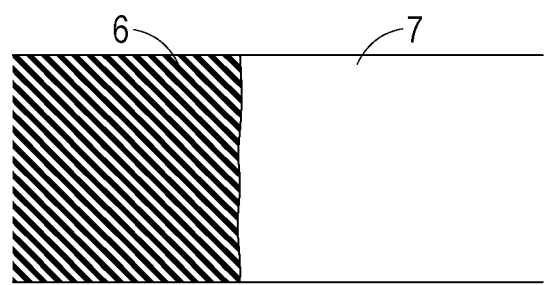

FIGS. 1A and 1B are schematic cross-sectional views of a configuration of an embodiment of an X-ray generating apparatus 100 of the present invention. FIG. 1A illustrates an X-ray generating tube 2 seen from a shielding member 9 side and FIG. 1B illustrates a cross-section of an X-ray generating tube 2 including a tube axis. FIGS. 2A and 2B are enlarged views of an area in which an insulating member 6 and a third window 7 face each other. A configuration in which a transmissive X-ray generating tube 2 is used in this example, but a reflective X-ray generating tube is also applicable to the present invention.

An outer case 1 is a container in which the X-ray generating tube 2 is contained. The outer case 1 may be made of metal, such as iron, stainless steel, lead, brass, and copper. In the present embodiment, the X-ray generating tube 2 and a driving circuit 3 which applies a tube voltage and drives an electron source 10 in the X-ray generating tube 2 are contained in the outer case 1, and an unoccupied space of the outer case 1 is filled with an insulating fluid 4. The X-ray is generated when the X-ray generating tube 2 and the driving circuit 3 are connected by an unillustrated wire and the X-ray generating tube 2 is driven.

The insulating fluid 4 is used to provide insulation between the outer case 1 and the X-ray generating tube 2 and to cool the X-ray generating tube 2. Cooling by the electro hydro dynamics (EHD) phenomenon is efficient. The EHD is a phenomenon that an insulating liquid or gas begins to flow between electrodes when a tube voltage is applied to the insulating liquid or gas. In the present embodiment, a flow by the EHD may be produced by a tube voltage applied to the X-ray generating tube 2, and the insulating fluid 4 may circulate in the outer case 1. Insulation oils, such as mineral oil and silicone oil, are especially desirable as the insulating fluid 4 from the viewpoint of the cooling efficiency. As other examples of the insulating fluid 4, insulating gases, such as nitrogen and sulfur hexafluoride ($SF_6$) may be circulated by a suitable convection generation means to obtain a cooling effect.

The outer case 1 has an opening 1a which is closed by a second window 5. X-ray 14 from the X-ray generating tube 2 passes from the outer case 1 through the second window 5. When the second window 5 is not in place, the third window 7 can be removed through the opening 1a and the insulating fluid 4 can be added or removed from the outer case 1. The second window 5 is made of a material with relatively smaller X-ray attenuation, such as acrylics, polycarbonate, aluminum, beryllium, and glass.

Figure 3:
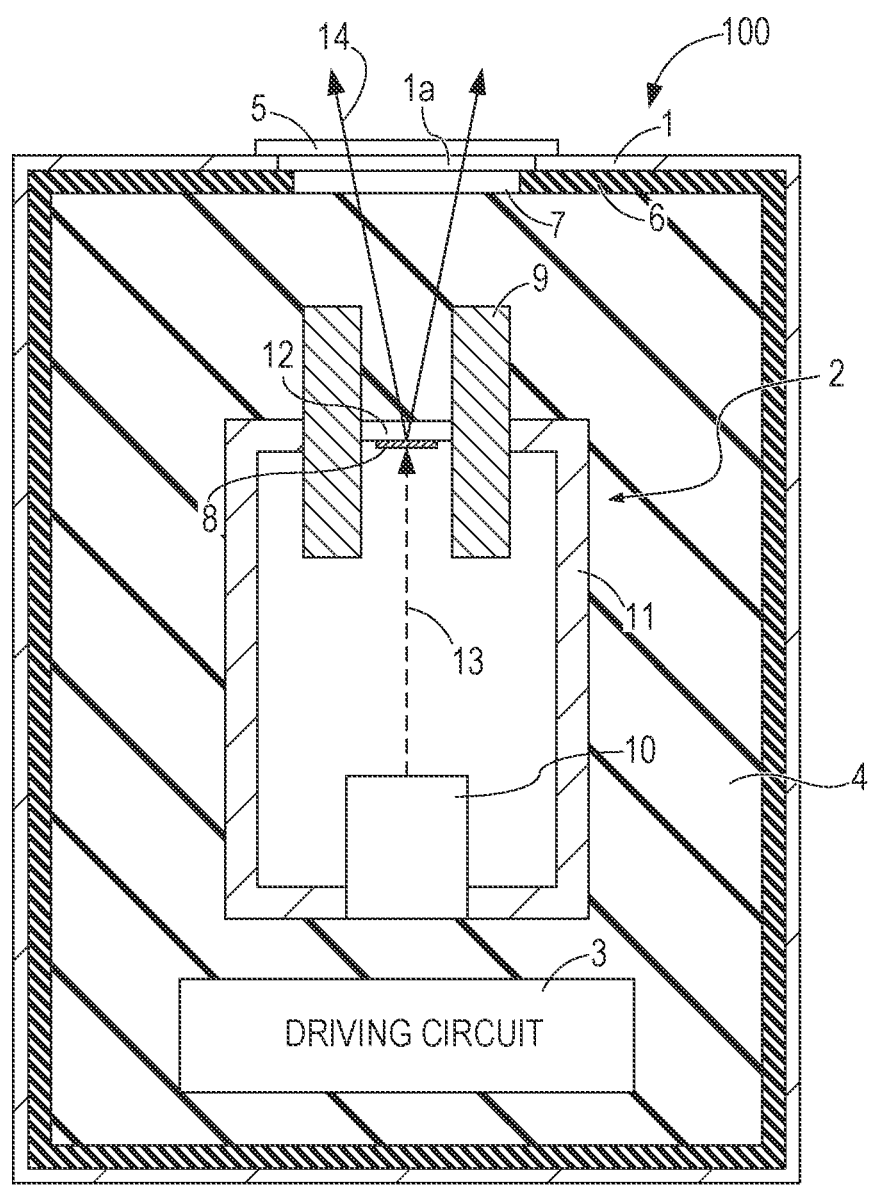
FIG. 3 is a schematic cross-sectional view of a configuration of another embodiment of an X-ray generating apparatus of the present invention, illustrating a cross-section of an X-ray generating tube including a tube axis.

In the present invention, the third window 7 and the insulating member 6 are located with a space from the first window 12 between the second window 5 of the outer case 1 and the first window 12 of the X-ray generating tube 2 in order to increase voltage withstanding property between the outer case 1 and the X-ray generating tube 2. The third window 7 and the insulating member 6 in this example are located in contact with the outer case 1 and close the opening 1a of the outer case 1. The third window 7 removably fits into an opening of the insulating member 6. This means that the insulating member 6 is also a frame material for fixing the third window 7, and an outer periphery of the third window 7 is surrounded by the insulating member 6. The insulating member 6 is formed only on a surface of the outer case 1 on the side on which the second window 5 is attached in this example, but the insulating member 6 may be provided on the entire inner surface of the outer case 1 as illustrated in FIG. 3.

In the present invention, the third window 7, i.e., the opening of the insulating member 6, corresponds to an X-ray irradiation area. In the present invention, since the third window 7 removably fits into the opening of the insulating member 6, only the third window 7 may be removed and replaced easily.

In the present invention, the third window 7 has a linear expansion coefficient greater than that of the insulating member 6.

In the present invention, the third window 7 and the first window 12 face each other via a gap through which the insulating fluid 4 is flowable. Therefore, when the X-ray generating tube 2 that generates the X-ray 14 is driven, the insulating fluid 4 conducts heat generated in the X-ray generating tube 2 to the entire outer case 1 by, for example, the EHD phenomenon. Therefore, the temperature of the parts inside the outer case 1 rises equally. When the X-ray generating tube 2 is not driven, during which X-ray 14 is not generated, the third window 7 and the insulating member 6 are not in contact with their ideal surfaces but with many points in accordance with process tolerance as illustrated in FIG. 2A. When the X-ray generating tube 2 is driven, during which the temperature of the insulating member 6 and the third window 7 has risen equally, the insulating member 6 and the third window 7 have a thermal expansion difference due to a difference in a linear expansion coefficient, whereby surfaces of the insulating member 6 and the third window 7 elastically deform and increase adhesiveness therebetween as illustrated in FIG. 2B. This provides an effect that electrical discharge through the gap between the insulating member 6 and the third window 7 is reduced when the X-ray generating tube 2 is driven.

A preferred embodiment of the present invention is that the third window 7 is in contact with the insulating fluid 4 on the side on which the third window 7 faces the second window 5. Since the third window 7 is in contact with the insulating fluid 4 on the front and back sides thereof, the difference in temperature in the thickness direction of the third window 7 decreases, whereby adhesiveness between the insulating member 6 and the third window 7 further increases when the X-ray generating tube 2 is driven. Specifically, it is only necessary to attach the insulating member 6 to the outer case 1 with the insulating member 6 separated from the outer case 1 with a gap through which the insulating fluid 4 flows.

When driving of the X-ray generating tube 2 is stopped, the temperature of the insulating member 6 and the third window 7 is lowered and the insulating member 6 and the third window 7 return to the state illustrated in FIG. 2A. In this state, the third window 7 can be removed easily from the insulating member 6. If the third window 7 fits into the insulating member 6 loosely, the third window 7 may be fixed to the insulating member 6 at several peripheral portions with an adhesive as long as the third window 7 can be removed.

In the present invention, the difference in the linear expansion coefficient between the insulating member 6 and the third window 7 is preferably equal to or greater than $1 \times 10^{-5}/°$ C. to equal to or less than $20 \times 10^{-5}/°$ C. In this range, both effects of removal of the third window 7 and provision of voltage withstanding property are achieved desirably.

In the present invention, the amount of X-ray absorption of the third window 7 that the X-ray 14 transmits is desirably small. The amount of X-ray absorption is represented by the product of the X-ray absorption coefficient of the member and the thickness of the member in the X-ray transmission direction. Therefore, in the present invention, the product of the X-ray absorption coefficient and the thickness of the third window 7 is desirably smaller than the product of the X-ray absorption coefficient and the thickness of the insulating member 6. The thickness of the third window 7 is the thickness in the transmission direction of the X-ray 14 from the X-ray generating tube 2, and the thickness of the insulating member 6 is the thickness in the tube axial direction of the X-ray generating tube 2 in the this example. In the present invention, it is only necessary to satisfy any or both of the following conditions: the third window 7 is made of a material with the X-ray absorption coefficient smaller than that of the insulating member 6; or the thickness of third window 7 is set to be smaller than that of the insulating member 6.

In the present invention, an image with high contrast is obtained by shielding unnecessary X-ray with the insulating member 6 while providing the amount of X-ray taken out of the third window 7. In the medical X-ray inspection, photographing is conducted at the X-ray energy of about 40 keV to 120 keV. Therefore, when the relationship between the product of the absorption coefficient and the thickness satisfies the above energy range, the contrast of the photographed image increases and the image is valid in respect of inspection accuracy. Further, the X-ray generating apparatus 100 used at home or disaster sites, it is desirable that the X-ray energy satisfies the above condition in the range of 70 keV to 120 keV in order to diagnose characteristic parts, such as the chest and the abdomen. It is also desirable that the X-ray energy satisfies the above condition in each energy value of 70 keV and 120 keV.

In the present invention, it is desirable that the integrated value of the X-ray absorption coefficient of the third window 7 is smaller than the integrated value of the X-ray absorption coefficient of the insulating member 6 in the range that the X-ray energy is 40 keV to 120 keV. It is also desirable that the integrated value of the X-ray absorption coefficient of the third window 7 is smaller than the integrated value of the X-ray absorption coefficient of the insulating member 6 in the range that the X-ray energy is 70 keV to 120 keV. Alternatively, it is desirable that the X-ray absorption coefficient of the third window 7 is smaller than the X-ray absorption coefficient of the insulating member 6 in at least one that the X-ray energy is 70 keV and 120 keV.

In the present invention, as a function other than the electrical voltage withstanding property, a function as a frame that fixes the X-ray generating tube 2 and the driving circuit 3 can be provided to the insulating member 6. The insulating member 6 is made of resin in order to achieve both rigidity and lightweight as the fixing frame. The third window 7 is also made of resin from the viewpoint of adhesiveness to the insulating member 6. The polymer compound such as resin, however, causes a chemical reaction due to X-ray irradiation and, as a result of a change in the molecular structure by the continuous X-ray irradiation, mechanical and electrical characteristics change. Mechanical changes due to X-ray irradiation include occurrence or development of cracks and defects. With the configuration of the present invention, the third window 7 is irradiated with the X-ray in the greatest amount, and the cracks and defects produced in the third window 7 due to the X-ray irradiation become the locations at which electrical discharge easily occurs. Therefore, in the present invention, the third window 7 desirably has X-ray resistance. As a guide of the X-ray resistance, the amount of X-ray irradiation at which breaking strength reduces by half is used and, in the present invention, 0.2 MGy or greater is preferable and 0.4 MGy or greater is more preferable at which the amount of X-ray irradiation at which breaking strength of the third window 7 reduces by half.

As described above, the third window 7 and the insulating member 6 according to the present invention is desirably made of resin. Specifically, acrylic resin, such as polyimide and polymethylmethacrylate (PMMA), polypropylene (PP), glass epoxy, and the like are used. Since the linear expansion coefficient, the X-ray absorption coefficient, and the X-ray resistance of these resins vary depending on the structure, the polymerization degree, and the like of the resins, it is only necessary to select a resin material that provides desired characteristics. In particular, since polyimide generally is high in linear expansion coefficient and X-ray resistance and low in X-ray absorption coefficient, the third window 7 is desirably made of polyimide. The insulating member 6 is made of acrylic resin, PP, or glass epoxy.

Figure 4A:
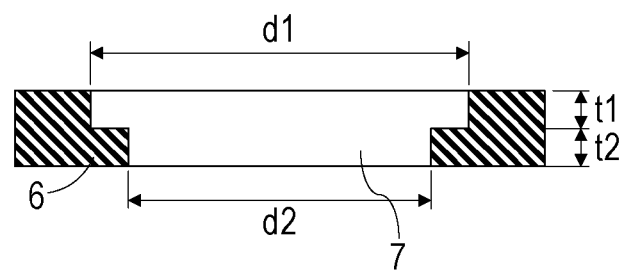
FIGS. 4A & 4B are schematic sectional views illustrating another example of a configuration of a third window according to the present invention.
Figure 4B:
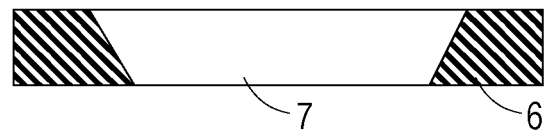

In the present invention, in order to improve voltage withstanding property of the outer case 1 and the X-ray generating tube 2, it is desirable that the thickness of the third window 7 is shorter than the length of an area in which the third window 7 and the insulating member 6 face each other (facing area) in the cross-section of the third window 7 and the insulating member 6 in the transmission direction of the X-ray 14. Voltage withstanding property improves by lengthening the electrical discharge path. The electrical discharge path which is the problem of the present invention is a path from the X-ray generating tube 2 to the outer case 1 via the gap between the third window 7 and the insulating member 6. Since the path includes the facing area as described above, voltage withstanding property can be improved by lengthening the facing area as in this configuration. During generation of the X-ray, the gap between the third window 7 and the insulating member 6 is narrowed due to thermal expansion, whereby voltage withstanding property further improves. Specifically, as illustrated in FIG. 4A, it is desirable to form a step on the facing surface of the third window 7 and the insulating member 6, or to provide the facing surface of the third window 7 and the insulating member 6 a taper shape as illustrated in FIG. 4B. In any case, the third window 7 and the insulating member 6 are disposed in a manner such that the area of the opening of the insulating member 6 is smaller than on the first window 12 side than on the second window 5 side.

Next, the X-ray generating tube 2 is described. As known to skilled artisans, the outer case is generally grounded for safety. Conventionally, there are at least 3 grounded manners named "cathode grounded manner", and "anode grounded manner" typically adapted for a monopolar voltage source and "neutral grounded manner" typically adapted for a bipolar voltage source. Which type grounded manner would be selected depends on various factors including a voltage source type, a size of an outer case, a voltage source, a discharge dielectric strength etc.

However, in the technical field of a transmission type X-ray generating tube, an anode grounded manner or a neutral grounded manner is typically adapted. The neutral point (common electrode) of the bipolar tube voltage circuit and the outer case are grounded in a neutral grounded manner. The neutral grounded manner especially allows decreasing a distance between the outer case and the anode (end window) and a distance between the outer case and the cathode. the outer case is more compact. In the X-ray generating tube 2, the electron source 10 and a target layer 8 face each other in a vacuum chamber 11. Electrons 13 emitted from the electron source 10 by a tube voltage applied between the electron source 10 and the target layer 8 enter the target layer 8 and generate X-ray 14. If the X-ray generating tube 2 is a transmissive tube and a potential difference is produced between the target layer 8 and the outer case 1, electrical discharge easily occurs between the X-ray generating tube 2 and the outer case 1. The potential of the outer case 1 is usually set to the ground potential. If a bipolar power supply system in neutral grounded manner is employed as a drive system of the X-ray generating tube 2, the potential of −Va/2 is applied to the electron source 10 and +Va/2 is applied to the target layer 8 (Va: tube voltage). The potential of the target layer 8 is applied via the shielding member 9 from the driving circuit 3. The potential of the target layer 8 becomes +Va/2, a potential difference of Va/2 is produced between the target layer 8 and the outer case 1 of which potential is the ground potential. Therefore, electrical discharge easily occurs between the shielding member 9 and the outer case 1. In the power supply system in neutral grounded manner, the potential applied to the target layer 8 is not limited to one half of the tube voltage, and includes a case in which the potential becomes positive with respect to the ground potential. As described above, the present invention can prevent electrical discharge also in the case in which the potential of the target layer 8 is defined to be positive with respect to that of the outer case 1. An electrical connection between the target layer 8 and the shielding member 9 is conducted via an unillustrated connecting electrode, or directly between some parts or all of the periphery of the target layer 8 and the shielding member 9.

The electron source 10 includes a form controllable from the outside since it has a plurality of nodes, such as an electron emitting portion which emits electrons, a heater which heats the electron emitting portion, a lead-out electrode which controls a leading state of the electrons, and a focusing electrode which shapes the lead-out electrons into a beam. There is a potential difference about 1 kV at the maximum between a plurality of nodes the electron source 10. The potential difference between nodes of the electron source 10 is low enough to the tube voltage Va.

Therefore, for example, if the potential applied to the target layer 8 is ½ of the tube voltage, a potential in the range of −1−Va/2 (kV) to +1−Va/2 (kV) is permitted for a plurality of potentials of the cathodes including the electron source 10 and, similarly, the potential in the range of −1+Va/2 (kV) to +1+Va/2 (kV) is permitted for the potential of the anodes including the target layer 8.

The neutral grounded manner is desirable in that since the absolute value of the voltage of the target layer 8 and the voltage of the electron source 10 to the ground potential can be made small, the driving circuit 3 can be reduced in size as compared with the case in which the potential of the target layer 8 is set to the ground potential. Considering from the dielectric breakdown distance of the insulating liquid 4, the outer case 1 may be generally reduced in size. In the present invention, the distance between the third window 7 and the shielding member 9 may be shortened.

The electron source 10 may be a hot cathode, such as a tungsten filament and an impregnated cathode, or a cold cathode, such as a carbon nanotube. The target 8 may be desirably made of a material with high melting point and high X-ray generating efficiency. For example, tungsten, tantalum, and molybdenum may be used.

A vacuum chamber 11 keeps the X-ray generating tube 2 be vacuumed and is made of, for example, glass or ceramic. The degree of vacuum in the vacuum chamber 11 is desirably equal to or greater than $1 \times 10^{-8}$ Pa to equal to or less than $1 \times 10^{-4}$ Pa. The upper limit of the degree of vacuum is determined depending on the stability of the electron emission characteristic of the electron source 10, i.e., the residual life of the electron source 10, and the lower limit of the degree of vacuum is determined depending on the cost of the airtight container, the exhaust process, and the like.

The first window 12 is a substrate which supports the target layer 8 and transmits a part of the X-ray generated in the target layer 8. The first window 12 is desirably made of a material that has enough strength to support the target 8, is not likely to absorb the X-ray generated in the target 8, and has high thermal conductivity so as to quickly radiate the heat generated at the target 8. For example, diamond, silicon nitride, aluminum nitride, and beryllium, may be used.

The shielding member 9 shields an unnecessary portion of the X-ray generated in the target layer 8. The shielding member 9 is a hollow cylinder with the first window 12 joined to an inner wall thereof. The shielding member 9 is made desirably of a material with high X-ray absorptivity and high thermal conductivity. For example, tungsten, copper, lead, tantalum, or alloys thereof may be used.

Figure 5:
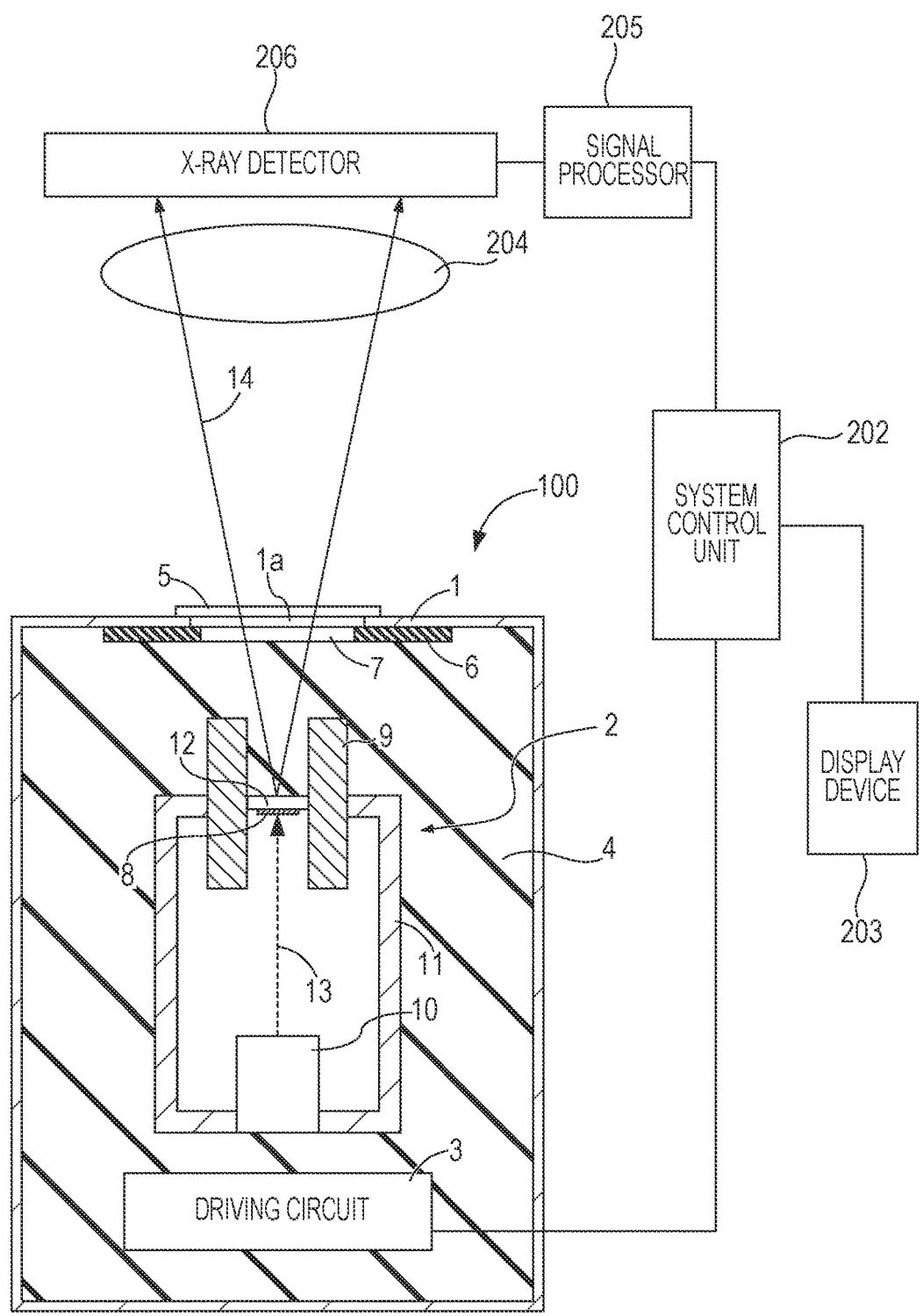
FIG. 5 is a schematic diagram of a configuration of a radiography system of the present invention.

Next, with reference to FIG. 5, an embodiment of a radiography system according to the present invention is described.

A system control unit 202 controls the X-ray generating apparatus 100 and an X-ray detector 206 in coordination with each other. The driving circuit 3 outputs various kinds of control signals to the X-ray generating tube 2 under the control by the system control unit 202. The driving circuit 3 is contained in the outer case 1 with the X-ray generating tube 2 in this example, but the driving circuit 3 may be disposed outside the outer case 1. A generation state of the X-ray 14 generated by the X-ray generating apparatus 100 is controlled by the control signals output by the driving circuit 3.

The X-ray 14 generated by the X-ray generating apparatus 100 is subject to adjustment of an irradiation area by an unillustrated collimator unit provided with movable diaphragm, emitted to the outside of the X-ray generating apparatus 100, penetrates the subject 204 and is detected by the X-ray detector 206. The X-ray detector 206 converts the detected X-ray into image signals, and outputs the image signals to a signal processor 205.

The signal processor 205 executes predetermined signal processing to the image signals under the control of the system control unit 202 and outputs the processed image signals to the system control unit 202. The system control unit 202 outputs display signals to a display device 203 in order to display an image on the display device 203 in accordance with the processed image signals. The display device 203 displays the image in accordance with the display signals on a display as a photographed image of the subject 204.

The radiography system of the present invention is applicable to non-destructive tests of industrial products and pathological diagnoses of human and animals.

EXAMPLES

Figure 6:
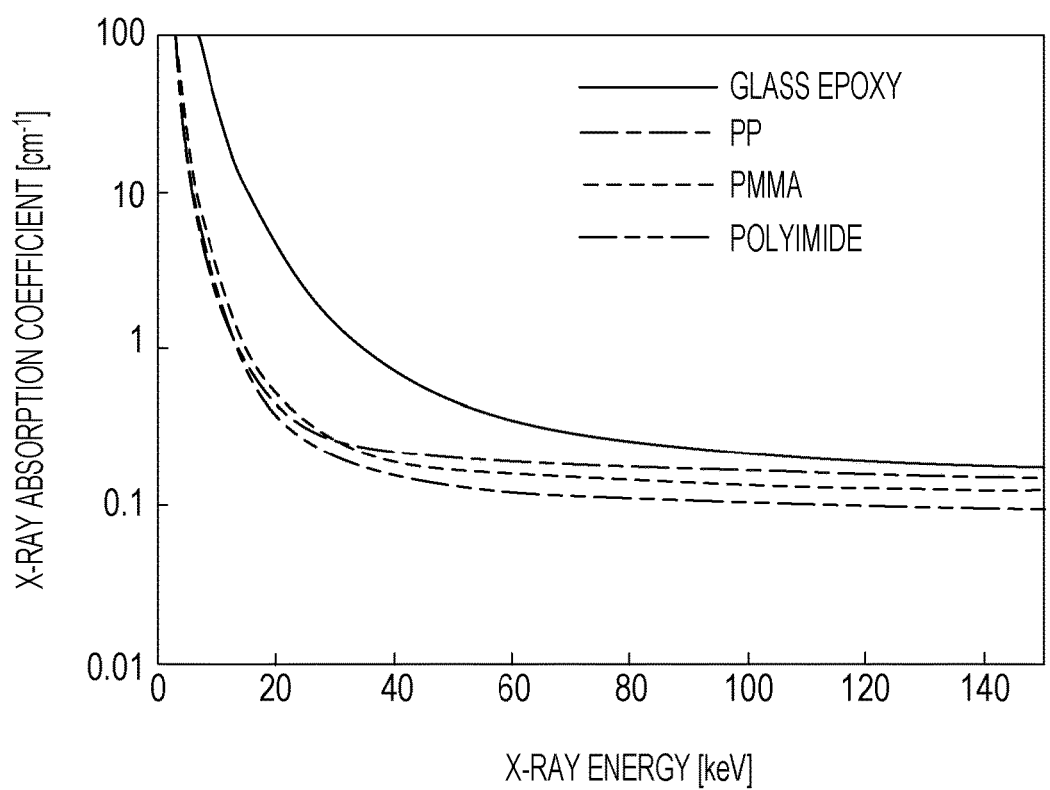
FIG. 6 illustrates an X-ray absorption coefficient of a resin material used in an example of the present invention.

Hereafter, examples of the present invention are described. The linear expansion coefficient and radiation resistance (the amount of X-ray irradiation with which breaking strength reduces by half) of a resin material used in the example are shown in Table 1 and the X-ray absorption coefficient is shown in FIG. 6. The linear expansion coefficient in Table 1 is measured in accordance with Japanese Industrial Standard K7197. The normalized dose of Each example is also shown in Table 1. The normalized dose is, when the X-ray generating tube of each Example is driven at the tube voltage of 100 kV, a dose value of the X-ray generated by the X-ray generating apparatus in the X-ray of which energy is 70 keV normalized with a dose value in Example 1.

Example 1

Regarding Example 1, the X-ray generating apparatus 100 illustrated in FIG. 3 is produced. In Example 1, the vacuum chamber 11 is an alumina cylinder which is 30 mm in inner diameter, 50 mm in outer diameter, and 80 mm in length. The electron source 10 is a thermal-electron gun of an impregnated cathode, is contained in the vacuum chamber 11, and is joined to the vacuum chamber 11 by silver soldering. As the target layer 8, tungsten which is 5 μm in thickness and 4 mm in diameter is selected and formed as a layer on one side of the first window 12 by CVD. To establish an electrical connection between the target layer 8 and the shielding member 9, a part of a peripheral portion of the target layer 8 is extended to a peripheral portion of the first window 12. As the first window 12, diamond which is 6 mm in diameter and 2 mm in thickness is selected. The shielding member 9 is a tungsten cylinder which is 6 mm in inner diameter, 30 mm in outer diameter, and 30 mm in length. The first window 12 is disposed in a manner such that a surface of the target layer 8 is located 10 mm away from the opening of the shielding member 9 on the electron source 10 side, and the inner wall of the shielding member 9 is joined to the peripheral portion of the first window 12 by silver soldering. The shielding member 9 is contained in and joined to the vacuum chamber 11 by silver soldering with the target layer 8 facing the electron gun 10 and an outer surface of the first window 12 being located on an extension of an outer surface of the vacuum chamber 11 on the third window 7 side. Then, air in the vacuum chamber 11 is exhausted to $10^{-7}$ Pa from an unillustrated exhaust pipe, and the exhaust pipe is sealed.

The outer case 1 is made of brass and 150 mm in width, 90 mm in depth, 150 mm in height, and 1 mm in thickness. The outer case 1 has the opening 1a which is 38 mm in diameter in one surface. The opening 1a is used as the second window 5 covered by a polycarbonate board which is 40 mm in diameter and 2 mm in thickness. The width of the outer case 1 corresponds to the left-right direction of the paper sheet in FIG. 1B, the depth corresponds to the vertical direction, and the height corresponds to the up-down direction.

As the insulating member 6, 4-mm-thick PMMA is selected and, as illustrated in FIG. 3, disposed to cover the entire inner surface of the outer case 1. The insulating member 6 has an opening which is 35 mm in diameter, and a PP plate which is 4 mm in thickness and 35 mm in diameter is inserted in the opening as the third window 7. The difference in the linear expansion coefficient between the third window 7 and the insulating member 6 in this example is $1\times10^{-5}/°$ C.

The X-ray generating tube 2 is contained in the outer case 1 with the third window 7 located 25 mm away from the first window 12 and a distance between the shielding member 9 and the third window 7 set to be 7 mm. Further, the driving circuit 3 is contained in the outer case 1 and connected with the X-ray generating tube 2 with an unillustrated wire. Mineral oil is selected as the insulating fluid 4. The vacuum deaerated insulating fluid 4 is injected from the opening 1a of the outer case 1, the second window 5 is disposed to cover the opening 1a of the outer case 1 from outside, and the second window 5 is fixed with an adhesive.

The X-ray generating apparatus 100 of this example is operated 20,000 continuous times with the tube voltage applied to the X-ray generating tube 2 being 100 kV, the tube current being 10 mA, the X-ray generation period being 0.1 seconds, and the quiescent period being 5 seconds. Application of the tube voltage is conducted in the neutral grounded manner in which one half of the negative voltage is applied to the electron source 10 and one half of the positive voltage is applied to the target layer 8 via the shielding member 9. The temperature of the insulating fluid 4 during continuous operation rises from the room temperature to 60° C. and is stable at 60° C. thereafter. When the electrical discharge counts during continuous irradiation are measured, no electrical discharge occurs. After the continuous operation, the second window 5 is removed and the third window 7 is taken out of the opening 1a of outer case 1 and replaced. When continuous irradiation is conducted under the same condition as that described above in the X-ray generating apparatus with a replaced third window 7, no electrical discharge occurs. Therefore, the third window 7 obtains both the effects of voltage withstanding property and replaceability in this example.

Example 2

An X-ray generating apparatus is produced to have the same configuration as that of Example 1 except that a step is formed in a contact surface of the third window 7 with the insulating member 6 as illustrated in FIG. 4A. In the third window 7, d1 is set to be 35 mm, d2 is set be 30 mm, and the thickness t1 of d1 and the thickness t2 of d2 are both 2 mm. The X-ray generating apparatus is driven under the same condition as that of Example 1 except that the tube voltage of a continuous operation condition is 120 kV. As a result, no electrical discharge occurs and the third window 7 is replaced without problems. In Example 2, an effect of higher voltage withstanding property than that of Example 1 is obtained.

Example 3

An X-ray generating apparatus is produced in the same manner as in Example 1 except that the third window 7 is formed of 4-mm-thick PMMA used for the insulating member 6 in Example 1 and the insulating member 6 is formed of a 4-mm-thick glass epoxy plate. As illustrated in FIG. 6, the X-ray absorption coefficient of PMMA used in this example is smaller than that of glass epoxy in the range of X-ray energy from 40 keV to 120 keV. Therefore, the integrated value of the X-ray absorption coefficient in that range is smaller in the third window 7 than in the insulating member 6 in this example. The product of the X-ray absorption coefficient and the thickness is also smaller in the third window 7 than in the insulating member 6. In this example, an effect is obtained that the third window 7 transmits the X-ray and unnecessary X-ray is absorbed by the insulating member 6. Since the X-ray absorption coefficient of the third window 7 is smaller in this example (PMMA) than in Example 1 (PP), a greater amount of dose may be taken.

The X-ray generating apparatus of this example is driven under the same condition as that of Example 1 with the tube voltage being 40 kV, 70 kV and 120 kV. As a result, no electrical discharge occurs during the operation and the third window 7 is replaced without problems after the quiescent period. When the dose value is measured near the second window 5, a greater amount of dose is obtained as compared with a case in which the third window 7 is made of PP as in Example 1: specifically, the dose is 105% in 40 kV, 110% in 70 kV, and 110% in 120 kV.

Example 4

An X-ray generating apparatus is produced in the same manner as in Example 3 except that 4-mm-thick polyimide is used as the third window 7. In this example, the continuous operation is conducted to check X-ray resistance. A continuous operation is conducted until the accumulated X-ray amount of the third window 7 becomes 0.4 MGy under the driving condition that the tube voltage of 120 kV, the tube current of 20 mA, the X-ray generation period of 1 second, and the quiescent period of 60 seconds. The electrical discharge is not counted during the continuous irradiation. The third window 7 after operation is taken out and observed to find no cracks. In this example, in addition to the effects of Examples 1 and 3, an effect of extending the replacement cycle is obtained by forming the third window 7 by a resin material with X-ray resistance.

TABLE 1

| MEMBER | RESIN MATERIAL | LINEAR EXPANSION COEFFICIENT ($\times 10^{-5}/°$ C.) | RADIATION RESISTANCE (MGy) | NORMALIZED DOSE (X-RAY ENERGY: 70 keV) |
|---|---|---|---|---|
| EXAMPLE 1 THIRD WINDOW | PP | 11 | 0.17 | 1.0 |
| INSULATING MEMBER | PMMA | 10 | 0.17 | |
| EXAMPLE 3 THIRD WINDOW | PMMA | 10 | 0.17 | 1.1 |
| INSULATING MEMBER | GLASS EPOXY | 7 | 3.6 | |
| EXAMPLE 4 THIRD WINDOW | POLYIMIDE | 16 | 17 | 1.1 |
| INSULATING MEMBER | GLASS EPOXY | 7 | 3.6 | |

Advantageous Effects of Invention

According to the X-ray generating apparatus of the present invention, when the X-ray generating apparatus is driven, electrical discharge resulting from a gap between the third window and the insulating member can be prevented while cooling the X-ray generating tube with the insulating fluid and, when the X-ray generating apparatus is not driven, the third window can be easily removed from the insulating member and replaced. Therefore, an X-ray generating apparatus and a radiography system of tube voltage withstanding property and high precision, easy in maintenance, and which can be used for a long period of time are provided.

While the present invention has been described with reference to exemplary embodiments, it is to be understood that the invention is not limited to the disclosed exemplary embodiments.

The scope of the following claims is to be accorded the broadest interpretation so as to encompass all such modifications and equivalent structures and functions.

This application claims the benefit of Japanese Patent Application No. 2015-147365, filed Jul. 27, 2015, which is hereby incorporated by reference herein in its entirety.

What is claimed is:

1. An X-ray generating apparatus, comprising:
an X-ray generating tube comprising a first window transmitting X-rays and configured to emit the X-rays through the first window;
an outer case configured to contain the X-ray generating tube and comprising a second window transmitting the X-rays at a position facing the first window;
an insulating fluid with which an unoccupied space of the outer case is filled;
an insulating member located between the first window and the second window and comprising an opening in an irradiation area of the X-rays through the first window; and
a third window removably fit into the opening of the insulating member, wherein
a linear expansion coefficient of the third window is greater than a linear expansion coefficient of the insulating member, and
the third window and the first window face each other via a gap in which the insulating fluid is flowable.

2. The X-ray generating apparatus according to claim 1, wherein a thickness of the third window is less than a length of an area in which the third window and the insulating member face each other in a cross-section in a transmission direction of the X-rays.

3. The X-ray generating apparatus according to claim 1, wherein a difference between the linear expansion coefficient of the third window and the linear expansion coefficient of the insulating member is equal to or greater than $1 \times 10^{-5}/°$ C. to equal to or less than $20 \times 10^{-5}/°$ C.

4. The X-ray generating apparatus according to claim 1, wherein the third window is in contact with the insulating fluid on the side on which the third window faces the second window.

5. The X-ray generating apparatus according to claim 1, wherein a product of the X-ray absorption coefficient and a thickness of the third window is less than a product of the X-ray absorption coefficient and a thickness of the insulating member.

6. The X-ray generating apparatus according to claim 5, wherein the X-ray absorption coefficient of the third window is less than the X-ray absorption coefficient of the insulating member.

7. The X-ray generating apparatus according to claim 5, wherein the thickness of the third window is less than the thickness of the insulating member.

8. The X-ray generating apparatus according to claim 5, wherein an integrated value of the X-ray absorption coefficient of the third window is less than an integrated value of the X-ray absorption coefficient of the insulating member in a range in which X-ray energy is 40 keV to 120 keV.

9. The X-ray generating apparatus according to claim 8, wherein an integrated value of the X-ray absorption coefficient of the third window is less than an integrated value of the X-ray absorption coefficient of the insulating member in a range in which the X-ray energy is 70 keV to 120 keV.

10. The X-ray generating apparatus according to claim 5, wherein a product of the X-ray absorption coefficient of the third window multiplied by the thickness of the third window is less than a product of the X-ray absorption coefficient multiplied by the thickness of the insulating member when the X-ray energy is 70 keV.

11. The X-ray generating apparatus according to claim 5, wherein a product of the X-ray absorption coefficient of the third window multiplied by the thickness of the third window is less than a product of the X-ray absorption coefficient multiplied by the thickness of the insulating member when the X-ray energy is 120 keV.

12. The X-ray generating apparatus according to claim 1, wherein an amount of X-ray irradiation at which breaking strength of the third window reduces by half is equal to or greater than 0.2 MGy.

13. The X-ray generating apparatus according to claim 12, wherein the amount of X-ray irradiation at which breaking strength of the third window reduces by half is equal to or greater than 0.4 MGy.

14. The X-ray generating apparatus according to claim 1, wherein the third window and the insulating member are made of resin.

15. The X-ray generating apparatus according to claim 14, wherein the third window is made of polyimide and the insulating member is made of acrylic resin, polypropylene, or glass epoxy.

16. The X-ray generating apparatus according to claim 1, wherein the X-ray generating tube is a transmissive tube, the X-ray generating tube comprising a target layer inside the first window, an electron source configured to emit electrons toward the target layer and the target layer is defined at a positive potential with respect to the outer case when the X-ray generating tube is driven.

\* \* \* \* \*